(12) United States Patent
Liu

(10) Patent No.: US 9,661,878 B2
(45) Date of Patent: May 30, 2017

(54) ELECTRONIC CIGARETTE

(71) Applicant: Tuanfang Liu, Ji'an (CN)

(72) Inventor: Tuanfang Liu, Ji'an (CN)

(\*) Notice: Subject to any disclaimer, the term of this patent is extended or adjusted under 35 U.S.C. 154(b) by 228 days.

(21) Appl. No.: 14/450,276

(22) Filed: Aug. 3, 2014

(65) Prior Publication Data

US 2016/0000145 A1    Jan. 7, 2016

(30) Foreign Application Priority Data

Jul. 3, 2014   (CN) .......................... 2014 1 0315237
Jul. 3, 2014   (CN) ..................... 2014 2 0366606 U

(51) Int. Cl.
*A24F 47/00*   (2006.01)
*A61M 15/06*   (2006.01)

(52) U.S. Cl.
CPC ........... *A24F 47/008* (2013.01); *A61M 15/06* (2013.01)

(58) Field of Classification Search
CPC ...... A24F 47/00; A24F 47/002; A24F 47/004; A24F 47/006; A61M 15/06; A61M 15/068
See application file for complete search history.

(56) References Cited

U.S. PATENT DOCUMENTS

| 2014/0041655 A1* | 2/2014 | Barron | ................. A61M 11/042 128/202.21 |
| 2015/0136157 A1* | 5/2015 | Liu | ....................... A61M 15/06 131/329 |
| 2015/0245661 A1* | 9/2015 | Milin | .................... A24F 47/008 131/329 |
| 2016/0044961 A1* | 2/2016 | Liu | ....................... A61M 15/06 131/329 |

\* cited by examiner

*Primary Examiner* — Anthony Calandra
(74) *Attorney, Agent, or Firm* — Matthias Scholl, PC; Matthias Scholl

(57) ABSTRACT

An electronic cigarette, including a mouthpiece assembly, a glass housing, a fixed seat, an atomization assembly, and a gas flow control assembly. The mouthpiece assembly employs a metal material and is connected to the fixed seat using a plug-type interference fit. The fixed seat is connected to the glass housing by means of screw thread. The atomization assembly is connected to the gas flow control assembly by means of screw thread, and is fixed on the fixed seat. The atomization assembly is disposed in the glass housing and includes heating wires. The heating wires are disposed at regular intervals and are vertical to the cylindrical surface of the glass housing.

2 Claims, 2 Drawing Sheets

ELECTRONIC CIGARETTE

CROSS-REFERENCE TO RELATED APPLICATIONS

Pursuant to 35 U.S.C. §119 and the Paris Convention Treaty, this application claims the foreign priority benefit of Chinese Patent Application No. 201410315237.9 filed Jul. 3, 2014 and Chinese Patent Application No. 201420366606.2 filed Jul. 3, 2014. The contents of all of the aforementioned applications are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to an electronic cigarette.

Description of the Related Art

It is well-known that smoking is harmful to health, but there are still hundreds of millions of smokers in the world, and the trend is continuing. To purify the environment, prohibition of smoking in public places has become the consensus. Thus, cigarette substitutes, such as patches for quitting smoking, nicotine mouthwash, nicotine gum, nicotine drink, flourish in the market. Although the cigarette substitutes are a step in the right direction as they do not deliver tar, nicotine is only slowly absorbed in the blood and thus the achieved effective peak concentration of nicotine is relatively low, and the feeling of satisfaction resulting from a high concentration of tobacco alkali is not achieved. Meanwhile, users consuming cigarette substitutes are deprived of smoking actions such as inhaling, exhaling, and puffing.

A conventional electronic cigarette employs a plastic cigarette holder and a plastic housing, and cannot regulate the air flow. Thus, the smoke volume cannot be adjusted according to personal preference. In use, a chemical reaction between the plastic materials and the tobacco tar may happen and produce harmful matters thereby polluting the environment and consumers. And the tobacco tar is difficult to load. In addition, the electrical contact of the electronic cigarette is rigid and has poor compatibility, which generally results in bad connection.

SUMMARY OF THE INVENTION

In view of the above-described problems, it is one objective of the invention to provide an electronic cigarette that features safe and environmentally friendly materials, convenient operation, high electrical compatibility, and the output volume of smoke is adjustable.

To achieve the above objective, in accordance with one embodiment of the invention, there is provided an electronic cigarette, comprising a mouthpiece assembly, a glass housing, a fixed seat, an atomization assembly, and a gas flow control assembly. The mouthpiece assembly employs a metal material and is connected to the fixed seat using a plug-type interference fit. The fixed seat is connected to the glass housing by means of screw thread. The atomization assembly is connected to the gas flow control assembly by means of screw thread, and is fixed on the fixed seat. The atomization assembly is disposed in the glass housing and comprises heating wires. The heating wires are disposed at regular intervals and are vertical to the cylindrical surface of the glass housing. The heating wires are disposed evenly and vertically in the glass housing so that the smoke oil is uniformly heated and evaporated.

In a class of this embodiment, the gas flow control assembly comprises an elastic electrode.

In a class of this embodiment, the glass housing comprises screw threads.

In a class of this embodiment, the heating wires are vertically disposed and coated with ceramic fiber paper for guiding oil. The inner bore of the heating wires contains no oil-guiding matters.

The working process of the electronic cigarette is summarized as follows. The heating wires are electrified and heated. The smoke oil in the glass bottle is evaporated and dispersed evenly by the heating wires. The gas flow control assembly regulates the output content of the smoke.

Advantages of the invention are summarized as follows: 1) The heating wires are disposed evenly and vertically in the glass housing and thus the smoke oil is uniformly heated and evaporated. 2) The gas flow of the electronic cigarette is adjustable, safe, and environmentally friendly.

BRIEF DESCRIPTION OF THE DRAWINGS

The invention is described hereinbelow with reference to accompanying drawings, in which.

DETAILED DESCRIPTION OF THE EMBODIMENTS

Figure 1:
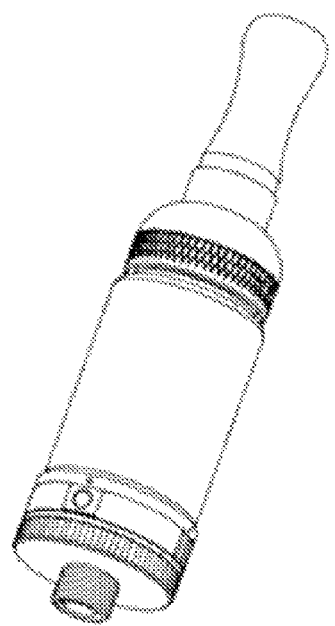
FIG. 1 is a schematic diagram of an electronic cigarette in accordance with one embodiment of the invention.
Figure 2:
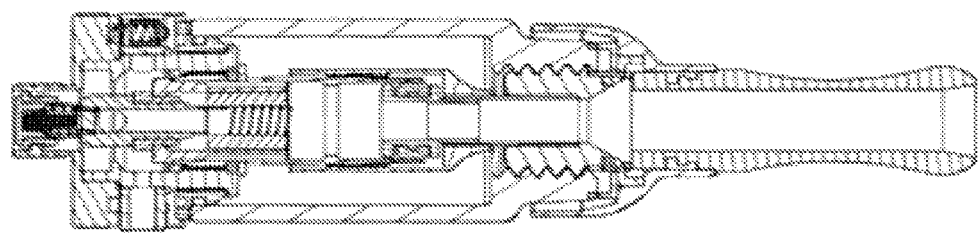
FIG. 2 is a sectional view of an electronic cigarette in accordance with one embodiment of the invention.
Figure 3:
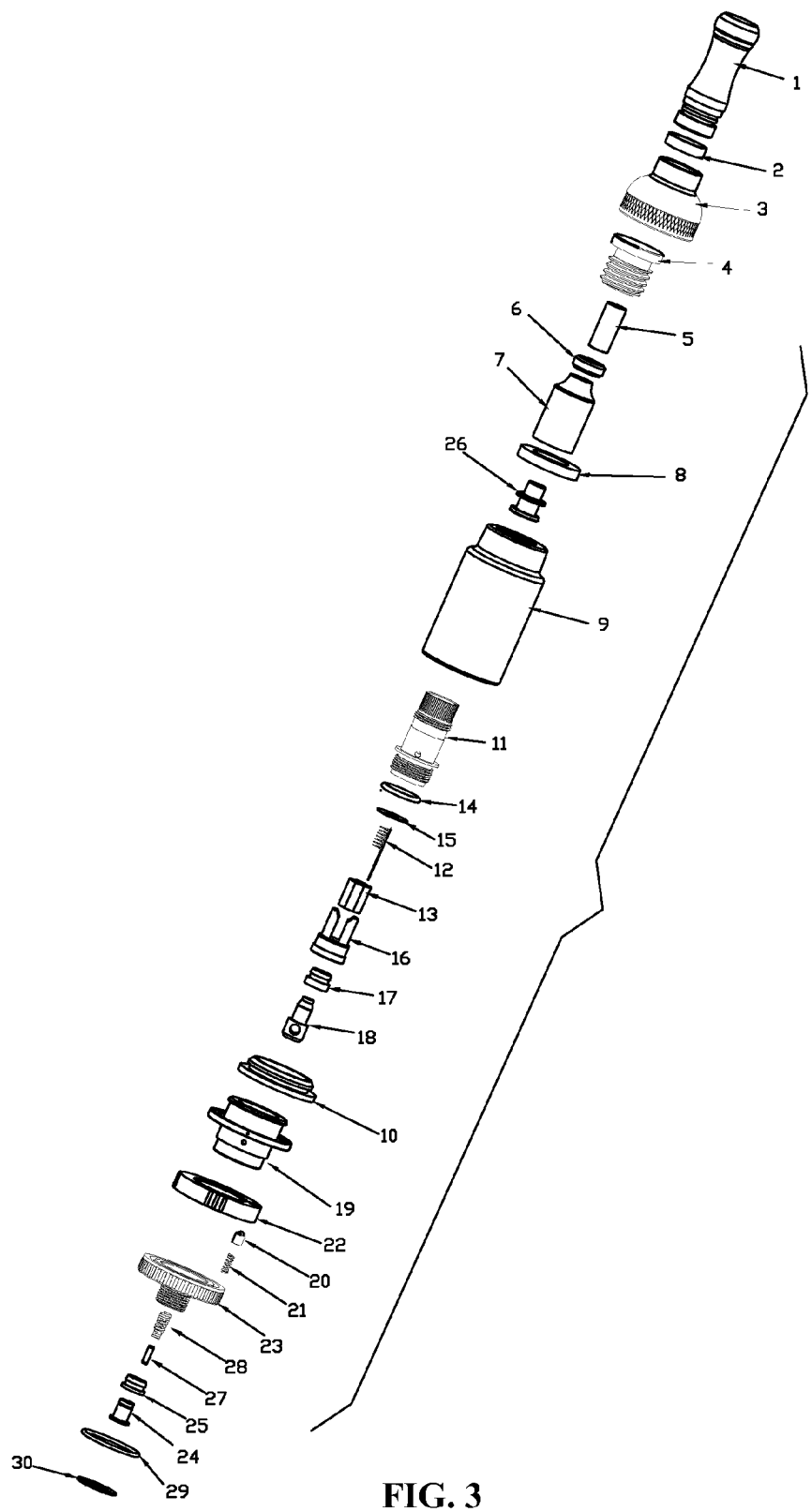
FIG. 3 is an exploded view of an electronic cigarette in accordance with one embodiment of the invention.

As shown in FIGS. 1-3, an electronic cigarette of the invention comprises a mouthpiece assembly, a glass housing, a fixed seat, an atomization assembly, and a gas flow control assembly. The mouthpiece assembly employs a metal material and is connected to the fixed seat using a plug-type interference fit. The fixed seat is connected to the glass housing by means of screw thread. The atomization assembly is connected to the gas flow control assembly by means of screw thread, and is fixed on the fixed seat.

The mouthpiece assembly comprises a cigarette holder 1 at the top thereof, a middle support 3, and a bottom rod 5. A sealing ring 2 is disposed between the cigarette holder 1 and the middle support 3. The bottom rod 5 is in fixed connection to the middle support 3 via a fixed screw 4, and an upper sealing gasket 8 is disposed in the fixed screw 4. The atomization assembly comprises, from the top down, a screw 7, a seal ring 6 of heating wires, a seal seat 26 of an atomization rod, a limit cover 11 of heating wires, a seal ring 14, a steel mesh 15, heating wires 12, oil guide cotton 13, cotton wool 31, a fixed ring 16 of the heating wires, an insulation ring 17 of the heating wires, and a joint 18. The glass housing comprises a glass bottle 9 and a sealing gasket 10 of the glass bottle. The gas flow control assembly comprises, from the top down, a gas flow control ring 19, a gas flow regulation ring 22, a section pin 20, a section spring 21, an outer copper thread ring 23, a jointing spring 28, a jointing pin 27, a jointing insulation ring 25, and a second joint 24. The bottom of the atomization assembly is sealed by a seal ring 29 of the outer copper thread ring and a seal ring 30 of the gas flow regulation ring.

The working process of the electronic cigarette is summarized as follows. The heating wires are electrified and heated. The smoke oil in the glass bottle is evaporated and dispersed evenly by the heating wires. The gas flow control assembly regulates the output content of the smoke.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An electronic cigarette, comprising:
a) a mouthpiece assembly;
b) a glass housing;
c) a fixed seat;
d) an atomization assembly; and
e) a gas flow control assembly;
wherein:
the mouthpiece assembly employs a metal material and is connected to the fixed seat using an interference fit;
the fixed seat is connected to the glass housing by means of screw thread;
the atomization assembly is connected to the gas flow control assembly by means of screw thread, and is fixed on the fixed seat;
the atomization assembly is disposed in the glass housing and comprises heating wires;
the heating wires are disposed at regular intervals and are vertical to the cylindrical surface of the glass housing;
the glass housing comprises screw threads; and
the heating wires are vertically disposed and coated with ceramic fiber paper.

2. An electronic cigarette, comprising:
a mouthpiece assembly;
a glass housing;
a fixed seat;
an atomization assembly; and
a gas flow control assembly;
wherein
the mouthpiece assembly employs a metal material and is connected to the fixed seat using a plug-type interference fit;
the fixed seat is connected to the glass housing by means of screw thread;
the atomization assembly is connected to the gas flow control assembly by means of screw thread, and is fixed on the fixed seat;
the mouthpiece assembly comprises a cigarette holder, a middle support, and a bottom rod;
a sealing ring is disposed between the cigarette holder and the middle support;
the bottom rod is in fixed connection to the middle support via a fixed screw, and an upper sealing gasket is disposed in the fixed screw;
the atomization assembly comprises, from the top down, a screw, a seal ring of heating wires, a seal seat of an atomization rod, a limit cover of heating wires, a seal ring, a steel mesh, heating wires, oil guide cotton, cotton wool, a fixed ring of the heating wires, an insulation ring of the heating wires, and a joint;
the glass housing comprises a glass bottle and a sealing gasket of the glass bottle;
the gas flow control assembly comprises, from the top down, a gas flow control ring, a gas flow regulation ring, a section pin, a section spring, an outer copper thread ring, a jointing spring, a jointing pin, a jointing insulation ring, and a second joint; and
the bottom of the atomization assembly is sealed by a seal ring of the outer copper thread ring and a seal ring of the gas flow regulation ring.

* * * * *